US008613702B2

(12) United States Patent
Feer et al.

(10) Patent No.: US 8,613,702 B2
(45) Date of Patent: Dec. 24, 2013

(54) DEVICE, APPARATUS AND METHOD FOR OBTAINING PHYSIOLOGICAL SIGNALS BY WAY OF A FEEDING TUBE

(75) Inventors: David L. Feer, Brookline, MA (US); Robert A. Feuersanger, Westford, MA (US); Brian D. Gross, North Andover, MA (US); Suzanne Kavanagh, Andover, MA (US); Eric D. Nelson, Hampton Falls, NH (US); Daniel A. Silber, Lexington, MA (US)

(73) Assignee: Koniklijke Philips N.V., Eindhoven (NL)

( * ) Notice: Subject to any disclaimer, the term of this patent is extended or adjusted under 35 U.S.C. 154(b) by 126 days.

(21) Appl. No.: 13/057,769
(22) PCT Filed: Aug. 11, 2009
(86) PCT No.: PCT/IB2009/053550
§ 371 (c)(1),
(2), (4) Date: Feb. 7, 2011
(87) PCT Pub. No.: WO2010/023579
PCT Pub. Date: Mar. 4, 2010

(65) Prior Publication Data
US 2011/0144481 A1   Jun. 16, 2011

Related U.S. Application Data

(60) Provisional application No. 61/092,468, filed on Aug. 28, 2008.

(51) Int. Cl.
| | |
|---|---|
| A61B 5/00 | (2006.01) |
| A61J 15/00 | (2006.01) |
| A61B 5/02 | (2006.01) |
| A61B 5/042 | (2006.01) |
| A61B 5/087 | (2006.01) |
| A61B 5/04 | (2006.01) |
| A61B 5/0402 | (2006.01) |
| A61B 5/0205 | (2006.01) |
| A61B 5/1459 | (2006.01) |
| G06F 19/00 | (2011.01) |

(52) U.S. Cl.
CPC .............. *A61J 15/00* (2013.01); *A61J 15/0011* (2013.01); *A61J 15/0073* (2013.01); *A61B 5/02* (2013.01); *A61B 5/0421* (2013.01); *A61B 5/0878* (2013.01); *A61B 5/04* (2013.01); *A61B 5/0402* (2013.01); *A61B 5/0205* (2013.01); *A61B 5/1459* (2013.01); *A61B 5/72* (2013.01); *A61B 2562/164* (2013.01); *G06F 19/34* (2013.01); *A61B 2562/222* (2013.01); *A61B 2562/223* (2013.01); *A61B 2562/224* (2013.01)
USPC ........... 600/301; 600/424; 600/380; 600/393; 600/323; 600/325; 600/342; 600/593; 600/509; 600/549; 600/537; 604/523; 604/534; 604/528; 604/28

(58) Field of Classification Search
None
See application file for complete search history.

(56) References Cited

U.S. PATENT DOCUMENTS

| | | |
|---|---|---|
| 4,176,660 A | 12/1979 | Mylrea et al. |
| 5,105,812 A | 4/1992 | Corman |

(Continued)

FOREIGN PATENT DOCUMENTS

DE   102004001626 A1   8/2005

(Continued)

*Primary Examiner* — Bill Thomson
*Assistant Examiner* — Marie Archer (57) ABSTRACT

A neonatal feeding tube (10) includes electronics and instrumentation for monitoring a neonate and for provides nourishment to the neonate. The tube (10) includes electrodes (20) for sensing ECG signals of the neonate. Thermistors (22, 24, 28, 30) are placed at various points along the tube (10) to measure the neonate's temperature at those points. Breathing effort is measured by calculating a pressure differential at two pressure ports (32, 34). Pulse and SpO$_2$ are measured at a fiber optic window (35). The electrodes (20), a distal electrode (64) and a light source (66) aid in helping a caregiver position the tip (12) of the tube (10) correctly in the stomach of the neonate.

15 Claims, 5 Drawing Sheets

(56) References Cited

U.S. PATENT DOCUMENTS

| | | | |
|---|---|---|---|
| 5,357,954 A * | 10/1994 | Shigezawa et al. | 600/339 |
| 5,413,111 A * | 5/1995 | Wilkinson | 600/537 |
| 5,810,741 A * | 9/1998 | Essen-Moller | 600/529 |
| 6,259,938 B1 * | 7/2001 | Zarychta et al. | 600/380 |
| 7,463,918 B2 | 12/2008 | Kim | |
| 2006/0036164 A1 * | 2/2006 | Wilson et al. | 600/424 |
| 2008/0177175 A1 | 7/2008 | Mottola et al. | |
| 2009/0137911 A1 * | 5/2009 | Sinderby et al. | 600/484 |
| 2009/0187164 A1 * | 7/2009 | Rowe | 604/529 |
| 2010/0030098 A1 * | 2/2010 | Fojtik | 600/549 |

FOREIGN PATENT DOCUMENTS

| | | |
|---|---|---|
| GB | 2254253 A | 10/1992 |
| WO | 9217150 A1 | 10/1992 |
| WO | WO9217150 * | 10/1992 |
| WO | 02103409 A2 | 12/2002 |
| WO | 2004065098 A1 | 8/2004 |
| WO | 2005115234 A1 | 12/2005 |
| WO | 2006015230 A2 | 2/2006 |
| WO | WO 2006060458 A1 * | 6/2006 |
| WO | WO 2007014400 A2 * | 2/2007 |
| WO | 2008072150 A1 | 6/2008 |

* cited by examiner

DEVICE, APPARATUS AND METHOD FOR OBTAINING PHYSIOLOGICAL SIGNALS BY WAY OF A FEEDING TUBE

CROSS REFERENCE TO RELATED APPLICATIONS

This application claims the benefit of U.S. provisional application Ser. No. 61/092,468 filed Aug. 28, 2008, which is incorporated herein by reference.

The present application relates to neonatal and pediatric care. It finds particular application with a feeding tube associated with the care of newborns, and will be described with particular reference thereto. It is to be appreciated, however, that many of the concepts are scalable to pediatric and adult applications, and are not limited to the aforementioned application.

When caring for newborn babies, the size of the patient is an obvious difference when compared to adult patients or other pediatric patients. Because the patient is so much smaller, instruments, sensors, and the like have to be redesigned to be used with newborn patients. This task is not obvious to those skilled in the art and this invention includes novel techniques to capture familiar vital signs.

Neonates that need tube feedings typically are also monitored electronically by a physiologic monitor. Such monitors use multiple electrodes and sensors adhered to the patient's chest and abdomen in order to capture ECG signals for calculating heart rate and for obtaining a respiration-impedance waveform for calculating respiration rate. Adhesion of skin electrodes is a problem for neonates. Not only must the adhesive have the proper electrical characteristics to transmit electrical signals, it also must adhere well enough to maintain adequate signal integrity despite motion artifacts. Also, due to poor skin development and the criticality for fluid balance in the presence of insensible water loss (evaporation), neonates are frequently maintained in humidity and temperature controlled incubators which not only compound the problem of electrode adhesion, but create a need to obtain a feedback signal for the thermoregulation apparatus typically found in the incubator. Each time an electrode or sensor falls off, a caregiver must intervene immediately, which increases the workload of the care giving staff, and is disruptive to the important sleep cycle of the neonate.

Further, the preterm neonate typically lacks skin integrity and the frail skin is subject to irritation and laceration as a result of applying adhesives or sensors. Removal of said electrodes or sensors for routine skin integrity checks and cleaning can further irritate the delicate skin of the neonate during removal. In practice, there is no perfect adhesive for a neonatal skin electrode. External electrodes and their cables also complicate routine care of the neonate (e.g., washing) and may be disturbing to parents trying to bond with the infant.

As with all intensive care patients, temperature changes can indicate fever or other medical situation requiring attention. In the case of premature neonates, however, the thermoregulatory system is not yet fully developed, so unlike the adult population, a neonate's temperature can go into crisis within minutes (as opposed to hours for an adult) and thus must be monitored closely. Consequently, routine and continuous temperature monitoring is conducted in the neonatal intensive care unit (NICU). This is typically done with a thermistor probe temporarily placed in the armpit, groin, or skin. These temperature sensors entail excessive stimulation for the neonate, a factor which is believed to negatively impact development. Often, NICU patients are kept in incubators. Opening and closing the incubator in order to maintain temperature signals makes it difficult to maintain desired air temperature control inside the incubator.

Also, size from infant to infant can vary immensely. Viable premature babies are much smaller than their full term counterparts, in both weight and length. In the case of a neonatal feeding tube, the size of the tube is tailored to the size of the infant. In order to accommodate a range of sizes of infants, different sizes of tubes are typically required so the tip of the feeding tube rests in the stomach. Moreover, as newborn babies grow rapidly, an infant's feeding tube may need to be changed and or repositioned during its stay.

During insertion of a new feeding tube, care must be taken and verification checks made to assure that the tube has followed the esophageal path to the stomach and not the bronchial path into the lungs. Further, the opening(s) in the tube must be properly positioned in the stomach, not the esophagus, and the end of the tube must terminate before reaching the bottom of the stomach. Incorrect positioning of the feeding tube can result in aspiration of stomach contents and feeding material into the lungs, which can lead to a life-threatening lung infection or injury.

The present application provides a new and improved feeding tube, which overcomes the above-referenced problems and others.

In accordance with one aspect, an esophageal feeding tube that incorporates at least one lumen (tube) for feeding and provides a pathway for nourishment from outside of a subject into the stomach of the subject. At least two, but optimally three or more uniformly or non-uniformly spaced electrodes are on the outside of the feeding tube for measuring cardiac and respiratory activity of the patient, of which at least two electrodes are used at any given time.

In accordance with another aspect, an improved method of inserting an esophageal feeding tube into a subject is provided. The feeding tube is inserted into the esophagus of the subject. The feeding tube is advanced to a position estimated to place the tip of the feeding tube in the stomach of the subject. Cardiac activity is sensed at all electrodes simultaneously and the SA node (cardiac pacing center) of the heart location is detected by equidistributed depolarization (equal positive and negative inflection through the isoelectric line cardiac cycle. Once this location is detected, the distance to the proper tip placement in the patient is a mathematical function of head circumference in the neonate and maybe in the pediatric patient and adult. The sensed cardiac activity is processed to compare relative strengths of the activity sensed. The relative strengths are analyzed to determine whether the feeding tube is properly placed, requires further advancement, or requires retraction.

In accordance with another aspect, a method of monitoring a subject is provided. A lumen is provided for nourishment from outside of the subject into the stomach of the subject. The lumen and electronic conductors may be integrally constructed or assembled and then encased in a jacket. At least two electrodes, needed to measure impedance for respiration rate calculations, are positioned along the outside of the feeding tube for measuring cardiac and respiration activity of the subject, of which at least two of the electrodes are active at any given time.

In accordance with another aspect, a method of monitoring a subject is provided. A lumen is provided for detecting pressure above and below the diaphragm thus enabling a pressure differential monitoring indicating respiration effort and aiding in respiration rate and respiration effort detection. As the tube is inserted, the differential pressure is monitored until a minimal, e.g., zero, differential pressure is sensed to indicate proper placement. In accordance with another aspect, a method of monitoring a subject's respiration is provided. A low-mass thermistor is provided for detecting rapid temperature changes in the hypopharynx and another below the diaphragm, thus enabling a flow mode and differential flow temperature monitoring to indicate respiration air flow rate and volume calculation indicating flow. This also aids in the detection of proper tube placement. As the tube is inserted, temperature changes are monitored to determine if the thermistor is in the esophagus or the trachea. As the tube enters the trachea, temperature fluctuation both at a single point and between 2 points and therefore a respiration signal is still detected; but if tube is in the esophagus, there is no delta temperature detected, therefore no respiration signal is seen.

An advantage of this design is the opportunity to similarly measure SpO2 insofar as esophageal SpO2 equals Core/central SpO2. Another advantage lies in esophageal temperature readings reflecting true core temperature as opposed to axillary temperature.

Another advantage lies in fact that the esophagus is a muscle that constricts along the feeding tube thus ensuring an adequate electrode contact and automated reading generation, obviating the need for caregiver intervention.

Another advantage is the measure of respiration effort and resulting respiration by way of a differential pressure signal as measured between the hypo pharynx and sub-diaphragmatically.

Another advantage lies in the proximity of the ECG signal acquisition to the cardiac muscle itself thus increasing the relative signal magnitude detected as compared to surface electrodes.

Another advantage lies in continuous real time data detection.

Another advantage is that the neonate or the neonate's environment does not need to be disturbed to take readings.

Another advantage lies in the elimination of adhesive electrodes associated with neonatal care.

Another advantage lies in compatibility with existing monitoring equipment.

Another advantage lies in the ability to manually and/or automatically correct tube positioning based on a plurality of signals detected through ECG, Temperature differential and pressure differential detected during the insertion process.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
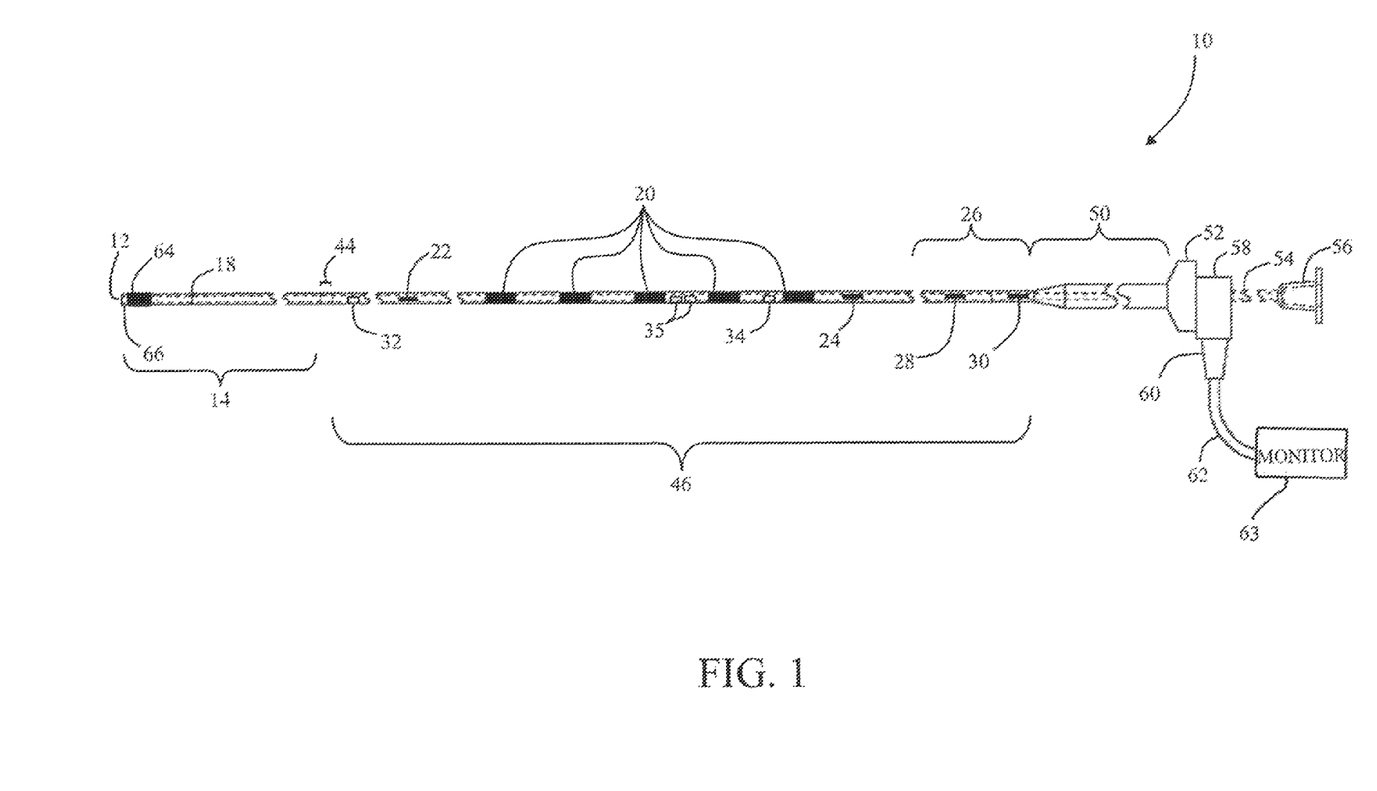
FIG. 1 depicts a neonatal feeding tube with instrumentation, in accordance with the present application.

With reference to FIG. 1, a neonatal feeding tube 10 is depicted. In one embodiment, the tube 10 is an instrumented disposable feeding tube for newborn infants (neonates) who have not yet developed their sucking capabilities, or who are unable to feed normally for some other reason. The tube 10 is a 5 French tube, or 1.67 mm in diameter, in one embodiment. Appropriate scaling can be performed for larger or smaller tubes. For convenience, the tube 10 is shown segmented, though its actual size is approximately 300 mm in length, for example.

Figure 2:
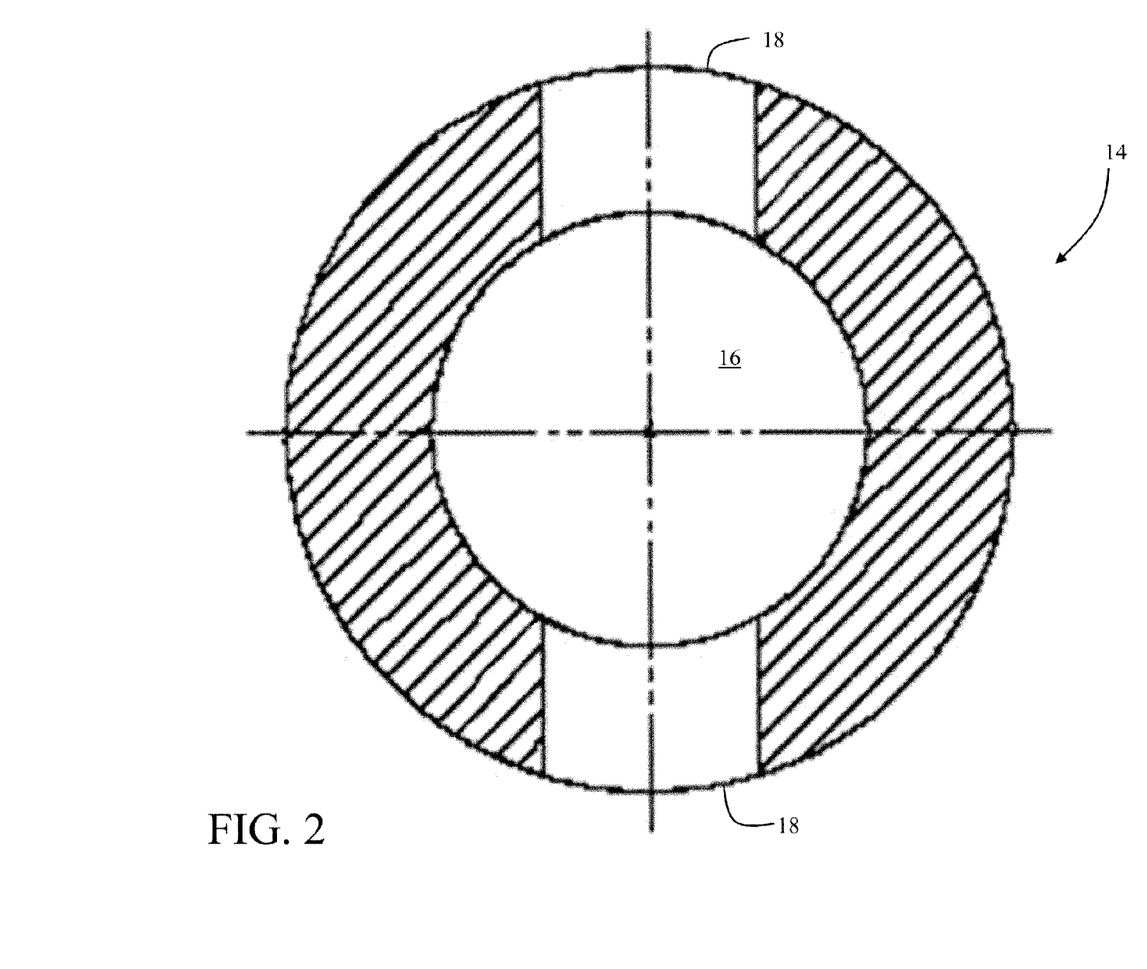
FIG. 2 is a cross sectional view of the feeding tube of FIG. 1 through a distal portion.

The neonates are fed formula or breast milk through the tube 10. The tube 10 is typically inserted into the nose or mouth and advanced into the esophagus, and into the stomach. Like a standard feeding tube, there is a tip 12 at the distal end of the tube. FIG. 2 depicts a cross sectional view of the distal portion 14. A hole 16 in the tip 12 permits food, such as infant formula or breast milk, to exit the tube. One or more additional holes 18, offset from the tip 12, allow feeding to exit in the event that the end hole 16 becomes clogged or otherwise blocked. The tip 12 and cross holes 18 are preferably located in the subject's stomach in one embodiment. The distal portion 14 is molded of a soft, biocompatible material, such as (in one embodiment) silicone rubber.

Figure 3:
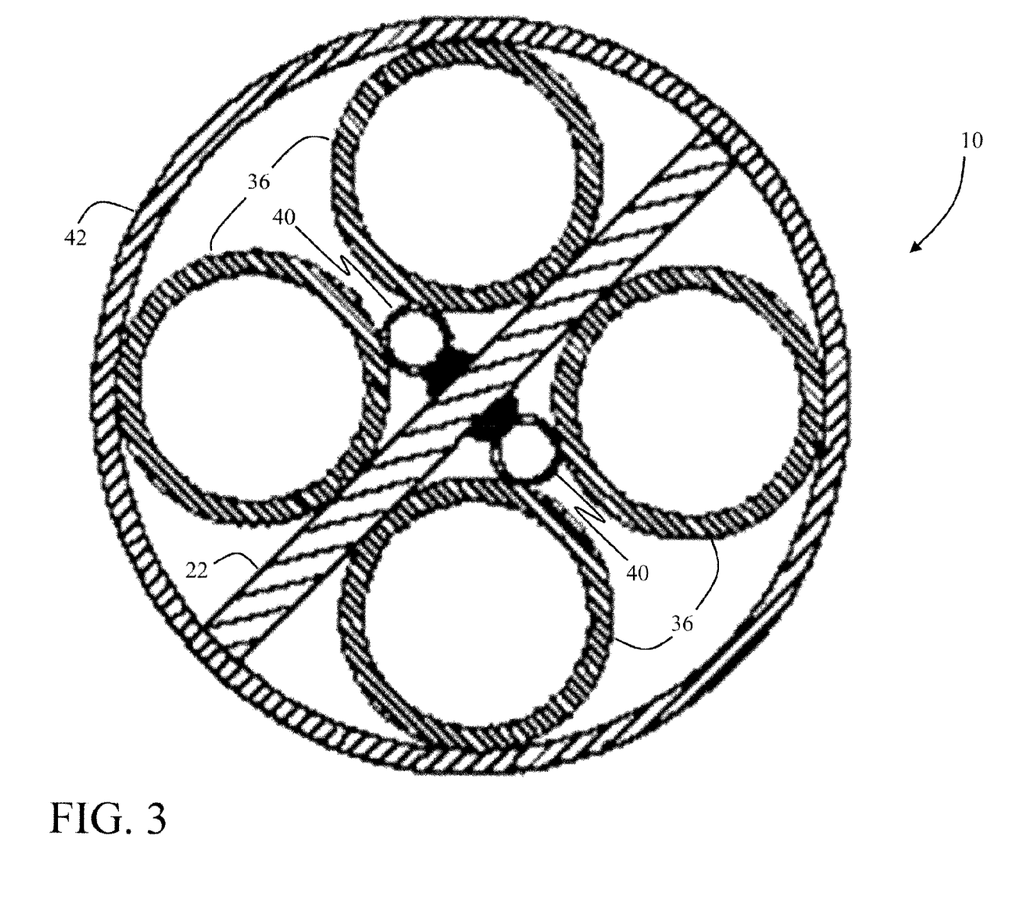
FIG. 3 is a cross sectional view of the feeding tube of FIG. 1 through a thermistor.

The feeding tube 10 also includes electrodes 20. The electrodes 20 are on an outside of the feeding tube and, when inserted, make contact with the subject's esophagus. Insulated leads extend proximally from each electrode, either inside the feeding tube 10 or the outer wall of the feeding tube. A thermistor 22 is inside the tube for taking temperature measurements and, in one embodiment, lies distal to the electrodes 20. FIG. 3 shows a cross section of the tube 10 including the thermistor 22 in cross-section.

The thermistor 22 is assembled to a pair of wires, at least one insulated. In one embodiment, the thermistor 22 is calibrated to meet the requirements of a specific patient monitor or series of monitors. Calibration is checked. Resistance is measured and compared to the specification. Resistance is then increased if necessary until the thermistor resistance meets specification. This process brings the thermistor in compliance with appropriate standards for accuracy. The thermistor 22 may be one piece of semiconductor material or it may be two or more segments connected in parallel, with a small gap between each segment. This allows the assembly to flex in two directions and to twist, even if the length is several multiples of the tube diameter. This is important, because the overall resistance of the thermistor is proportional to its thickness and inversely proportional to the area. Because the width of the thermistor and thickness of the thermistor are constrained by the size of the tube 10, the effective length of the thermistor assembly needs to be selected based on the electrical requirements of the monitoring system, without further constraint This method of construction also minimizes difficulty and discomfort during insertion, removal, and use. It is also more flexible and more resistant to breakage during manufacture, insertion, and use. In one embodiment, the thermistor 22 has a resistance of approximately $2250\Omega$ at 25° C. and approximately $1360\Omega$ at 37° C.

In a single-thermistor embodiment, the thermistor 22 is preferably located in the esophagus to accurately measure core temperature, rather than the stomach or pharynx, where readings would be less accurate. Placement in the stomach is undesirable due to the corrosive effects of gastric fluids and the inaccuracy that might be caused by air or food in the stomach. Whether the thermistor is located distal to the electrodes, proximal to them, or among them is determined by practical design issues and patient size. However, Dual lumen with at least 1 thermistor in the hypopharynx and can provide respiration measurement.

Proximal to the electrodes 20 is a nasopharyngeal section 26 of the feeding tube 10. The nasopharyngeal section 26, as the name indicates, lies inside the pharynx and nose when inserted. This section is smooth and small in diameter to avoid irritating the subject or interfering with air flow during breathing. In an alternate embodiment, however, it has a non-circular shape and/or concave flutes to reduce the possibility of complete blockage of a nare. In yet another embodiment, a hypopharynx thermistor 28 and an oropharynx thermistor 30 are included in the nasopharyngeal section 26. The thermistors 28, 30 are used to measure respiration flow, in addition the distal or caudal thermistor provides a core temperature measurement. The respiration flow is measured as a relative temperature change between the oropharynx thermistor 30 and the hypopharynx thermistor 28. An array of these thermistor pairs may accommodate variations of patient sizes.

A pressure differential ΔP is measured by a pressure gradient between a sub-diaphragmatic (or caudal) port 32 and a supra-diaphragmatic (or cephalic) port 34. ΔP represents the respiration effort of the subject. Flow can be measured separately (with thermistors 28 and 30), as an airway obstruction may produce increased effort but no ΔP. Respiration flow and respiration effort are measured separately and can differ. For example, in the case of an airway obstruction, effort will increase but flow will decrease. The measured flow can be cross-checked against ΔP for accuracy, and can signal an alarm if the two do not coincide.

Proximal to the supra-diaphragmatic pressure port 34 are two fiber optic window 35. The fiber optic windows are polished ends of many fiber optic strands. At the proximal end of the feeding tube the fiber optic strands separate into a source fiber (run from a light source, not shown) and a return fiber. Both fiber bundles run down the tube 10 to the fiber optic windows 35. One fiber optic bundle in esophagus and another at the distal tip of the feeding tube. The distal fiber bundle does not need to be separated into a sending and receiving bundle as it is used only to send light down which would emanate from the small patient due to the thin membranes and relatively translucent nature of the skin. This tip light is used for placement verification by energizing the fibers from an external light source and in a darkened room and visualizing the location of the light emanating from the patient's abdomen (if properly placed) or thorax (if not properly placed). The pulse of the subject is measured by reflectance photoplethysmogram through the fiber optic window using traditional reflectance pulse oximetry techniques. Core $SpO_2$ is also measured at the fiber optic window 35. The supra-diaphragmatic port 34 serves as a flush location to clean the fiber optic window 35 as needed.

Figure 4:
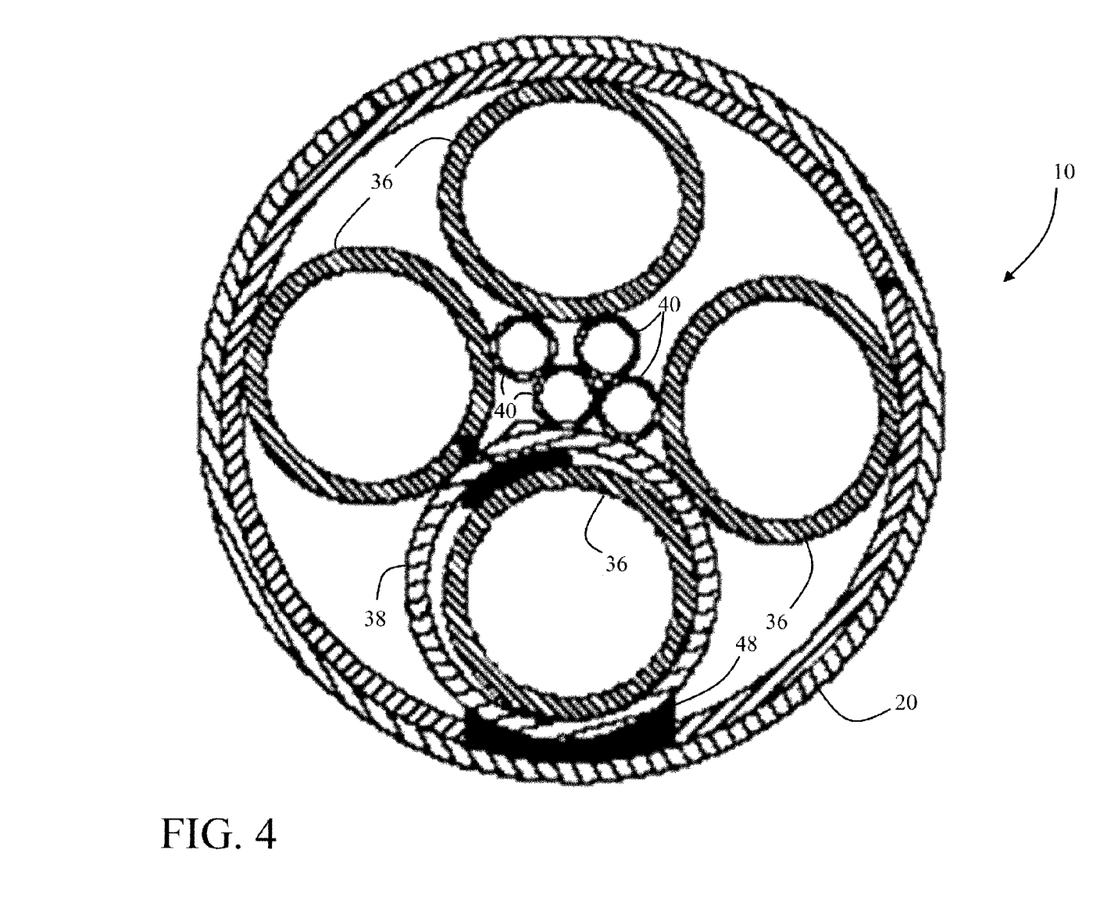
FIG. 4 is a cross sectional view of the feeding tube of FIG. 1 through an electrode.

With reference now to FIG. 4, and continuing reference to FIGS. 1-3, a possible method of manufacture is disclosed. In one embodiment, there are four feeding lumens 36. In a three-electrode embodiment, three of the four lumens 36 carry a contact for an electrode 20, and one lumen 36 does not. In a four-electrode embodiment, each of the four lumens 36 can carry a contact for an electrode 20. In a five-electrode embodiment, three of the four lumens 36 carry one contact while the fourth lumen 36 carries two contacts. Fewer or additional electrodes 20 can be positioned appropriately following the same pattern.

The lumens 36 are cut to length. At the appropriate location for each electrode 20, an un-insulated end of a wire is secured. In one embodiment, the wire is electrically and mechanically connected to a metal fitting 38 by soldering, welding, bonding with a conductive adhesive, crimping, or the like. The fitting 38 is then attached to the lumen 36 in the appropriate position, either by swaging, crimping, adhesive, or the like.

The lumen 36 and the thermistors 22, 24, 28, 30 are placed together with the thermistors 22, 24, 28, 30 and wires 40 in the center of the lumens 36, as depicted in FIG. 3. The distal portion 14 is brought together with the lumens 36 and thermistors 22, 24, 28, 30, held in place, and a jacket 42 is applied by extrusion, heat-shrinking, tape wrapping, or the like. The lumens 36 may reshape somewhat during this process, but this is inconsequential to the operation of the feeding tube 10. The wires 40 are preferably located in the center of the tube 10 for maximum flexibility. If additional bond strength is needed, a mechanical strength member (wire or fiber) can be added to the distal portion 14 and secured to the wires 40. A gap 44 between the distal portion 14 and a proximal portion 46 inside the jacket 42 serves as a blending area for flow from the multiple lumen 36 to blend and enter the distal part 14 and flow out the holes 16, 18 into the subject's stomach.

Next, the electrodes 20 are added. The jacket 42 is removed in the area of the electrode 20, as shown in FIG. 4. A conductive transition 48 such as a conductive adhesive, spring-like device, or the like is placed in the resulting removed area. An electrode 20, in the form of a short thin-wall cylinder, is placed over each conductive transition 48 and is then swaged to lock it in place. The proximal and distal edges are then bent into the jacket 42 to provide a smooth surface to reduce risk of injury to the patient.

Figure 5:
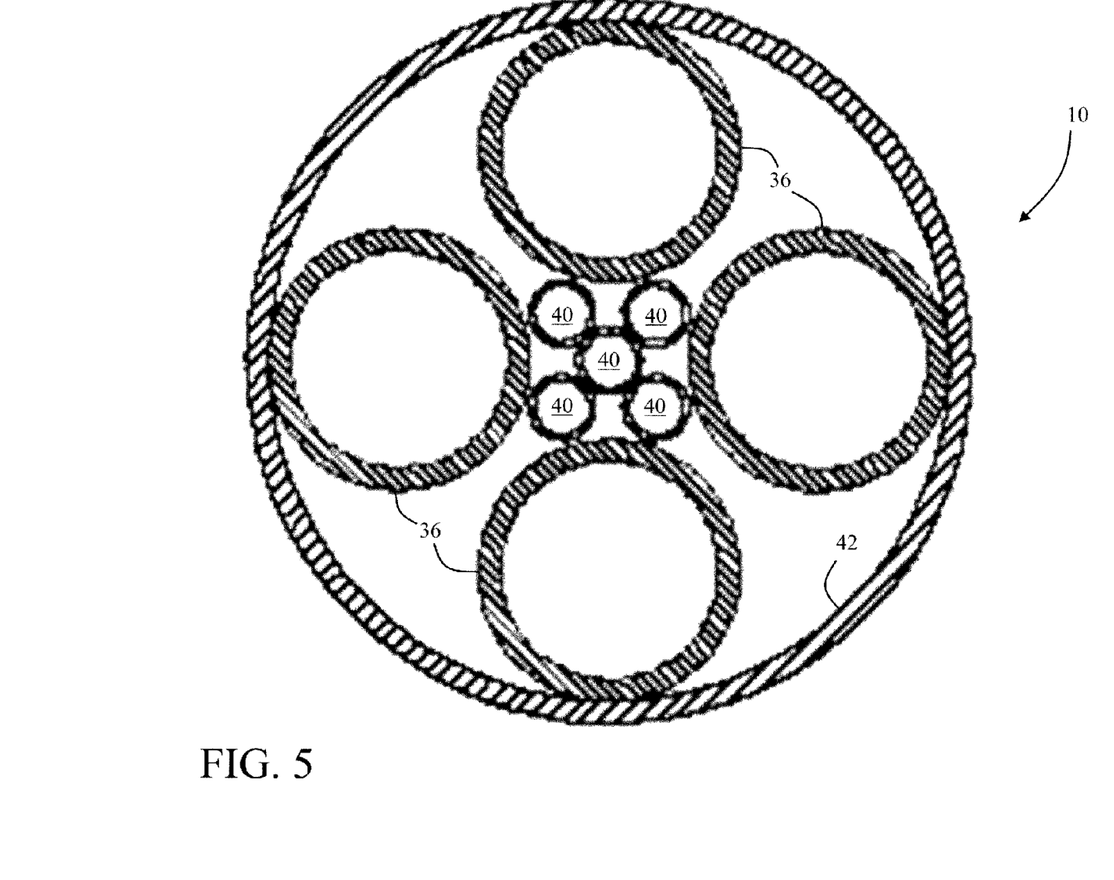
FIG. 5 is a cross sectional view of the feeding tube of FIG. 1 through a proximal portion.

An outside portion 50 of the tube 10 lies outside of the subject when the tube 10 is inserted. The outside portion 50 may have a larger cross section. The wires 40 that run from the components within the tube 10 terminate in a tube-side connector 52. A feeding lumen extension 54 may pass through the approximate center of the tube-side connector 52 and terminates in an oral style fitting 56 that permits baby formula or breast milk to be injected by syringe, drip, pump, or other means. In one embodiment, the fitting 56 is marked or physically differentiated to distinguish it from ports meant for vascular injection.

Mating with the tube-side connector 52 is a cable-side connector 58. In one embodiment, the cable-side connector 58 has a slot (not shown) that allows the cable-side connector 58 to be connected or disconnected without disturbing the feeding tube lumen extension 54. After passing through a flex relief section 60, external electrical wires 62 continue to a monitor 63. The external wires 62 may be fitted with an adapter that allows interface to various makes or models of patient monitors.

The outside portion 50, tube-side connector 52, feeding connector 56 and lumen extension 54 are secured using conventional insert molding, over-molding, and bonding techniques. An over-molded or assembled tube-side connector 52 mates with the cable-side connector 58 on the external wiring 62. The multiple feeding lumens 36 transition into a single lumen in the outside portion 50. The lumen extension 54 continues through openings in the connector parts 52, 58. In the lumen extension 54 there are no wires involved, and it is relatively transparent, which facilitates visual confirmation of flow. The lumen extension 54 is also flexible. If a caregiver needs to interrupt flow by pinching off the lumen, it should be done at the lumen extension 54. Once assembled, the feeding tube 10 is ready to be sterilized and packaged.

Typically, only three electrodes are required for ECG readings. For small neonates, the distal three electrodes 20 are used. For medium neonates, the middle three electrodes 20 are used. For larger neonates, the proximal three electrodes 20 are used. In one embodiment, the electrodes are selected manually based on the size of the neonate, and the judgment of the caregiver. The setting can be selected by the caregiver by temporarily disconnecting the connector, rotating the cable-side part 58 relative to the connector 52, and then re-connecting, thereby changing which internal contacts are used. In another embodiment, the electrodes are selected by the monitor 63. Once the tube is inserted, all electrodes 20 send signals to the monitor. The monitor displays multiple wave-forms, and the operator selects the clearest display. In other embodiments, all signals are recorded or the monitor automatically chooses the best electrodes.

It should be noted here that respiration rate can be determined by injecting a low-voltage electrical signal into the patient via a pair of spaced ECG electrodes. The electrical impedance of the connection varies during the act of respiration, so the rate and depth of respiration can be deduced. In some embodiments of this invention, the respiration rate is derived from a choice of electrodes selected from the array of available electrodes.

In an alternate embodiment a U-shaped connector on the monitor side is used so that the feeding tube 10 can be in the center, with mating in the axial direction. The U-shape allows the electrical connection and the feeding connection to be made or disconnected in any sequence, without mutual interference.

In another alternate embodiment, a connector is on the side of the feeding tube, with mating in the radial or oblique direction.

In another alternate embodiment, the tube 10 has a rectangular (linear) connector rather than a circular or U-shaped connector. In this embodiment, the feeding tube side would have a number of sockets (pins) equal to the number of electrodes, while the cable side would have a number of pins equal to the number of electrodes used by the monitor. The cable could then be plugged in to the feeding tube 10 in a number of locations, thereby selecting which electrodes are operative.

In another alternate embodiment, the tube 10 has a connector where the selection of the electrodes is performed by a switching device inside the cable-side connector 58, or the cable 62 itself.

In another alternate embodiment, the tube 10 has a connector with a rotating collar or other device which could be locked into place to assure that the connector, after disconnection, can only be re-connected in the selected position.

In another alternate embodiment, the tube 10 has a slide or rotary switch on the connector to allow the caregiver to manually select the electrodes with the strongest signal as shown on a monitor display.

Placing the tube properly can be problematic in some instances. The tube is to be inserted to a depth that places the tip 12 of the tube 10 in the stomach of the neonate. It is undesirable to insert the tube too far, into the duodenum, and it is also undesirable to leave it short, such that the openings 16 & 18 are in the esophagus. With reference again to FIG. 1, a distal electrode 64 on the tip 12 of the tube 10 is included to facilitate placement confirmation. While the distal electrode 64 remains in the esophagus, contact with the wall of the esophagus produces electrical continuity. However, when this electrode passes through the esophageal sphincter into the larger opening of the stomach, conductivity disappears. Because the relative location of the electrode 64 and the openings 18 is established by the detailed design of the device, the location of the openings 18 is now known to the clinician relative to the beginning of the patient's stomach.

In conjunction with the electrode 64, a light source 66 can be used to judge the position of the tip 12 as it is passed down the subject's esophagus. The neonate's chest is relatively thin and translucent. The light source 66, if bright enough, can be seen through the neonate's chest, and the caregiver can visually verify the position of the tip 12. The light source 66 may be illuminated by a lamp outside the proximal end and an optic fiber running the length of the tube 10. It is also contemplated that a fiber optic camera could be located at or fiber optically connected to the tip 12 and used as a traditional endoscope to aid in positioning the tube 10. In some embodiments, the fiber optic device is a permanent part of the tube 10; whereas, in alternative embodiments, the fiber optic device is inserted into a feeding lumen 36 prior to placement in the body and removed after the tube 10 is properly placed, so that the lumen 36 may be used for feeding.

When inserting the tube 10, it is important to follow the esophagus and not veer into the lungs. One way to tell which path is being followed is by a temperature measurement with thermistors at the tip 12. If different temperatures are measured with inhale and exhale respiration, the tip is in an air passage. If the temperature is constant, the tip is in the esophagus. Monitoring pressure at the tip can be used analogously. Pressure can be measured by sealing one of the lumens and adding a pressure port.

Another aid in positioning the tube 10 is to include a sensor that measures pH. If the tip 12 is properly in the stomach, the measured pH should be acidic. If the tip 12 is in the lungs, the measured pH will be neutral. If the tip 12 is in the esophagus, the measured pH will be somewhat acidic, depending on reflux, etc.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An orogastric or nasogastric feeding tube including:
   a tubular construction defining at least one lumen that provides a pathway for nourishment from outside of a subject into a stomach or small intestine of the subject;
   an oropharynx thermistor for monitoring a temperature of the subject in a region of the subject's pharynx;
   a hypopharynx thermistor for monitoring a temperature of the subject inferior to the pharynx of the subject; and
   a monitor which measures respiration flow rate from a relative temperature change between the oropharynx thermistor and the hypopharynx thermistor.

2. The orogastric or nasogastric feeding tube as set forth in claim 1, wherein the tubular construction includes at least one of:
   a molded or jacketed build-up of discrete parts including lumen, wires, electromechanical components;
   wires layered onto a center lumen that is over-molded, cast, or encapsulated after layering;
   molded in-wall wires in a single lumen or a multi-lumen extrusion; or
   a discrete bundle of wires installed into one of multiple lumens, the multiple lumens physically separate a feeding path in one of the lumens from the thermistors;
   wherein the wires are connected with the oropharynx thermistor and the hypopharynx thermistor.

3. The orogastric or nasogastric feeding tube as set forth in claim 1, further including:
   a plurality of lumens, a wiring bundle, and/or optical fiber bundles substantially in a center of the lumens.

4. The orogastric or nasogastric feeding tube as set forth in claim 1, further including:
   a supra-diaphragmatic pressure port for monitoring a pressure of the subject superior to the diaphragm of the subject; and
   a sub-diaphragmatic pressure port for monitoring a pressure of the subject inferior to the diaphragm of the subject.

5. The orogastric or nasogastric feeding tube as set forth in claim 4, wherein the monitor further implements an algorithm to:
from the pressure of the subject inferior to the diaphragm of the subject monitored with the sub-diphragmatic pressure port, calculate a change in pressure to generate a respiration effort signal.

6. The orogastric or nasogastric feeding tube as set forth in claim 1, wherein the monitor further implements the algorithm to:
measure cardiac activity waveforms measured by the electrodes; and
analyze the waveforms to determine when the feeding tube is located at a selected location, such as when the active electrode is adjacent an SA node to position the tip based on biometric or demographic information related to the patient, e.g. biometric information, age, gender, head circumference, or the like, and confirm that the tube is properly placed, should be further advanced, or should be retracted.

7. The orogastric or nasogastric feeding tube as set forth in claim 6, the monitor further implements the algorithm to:
select a subset of the electrodes that detect equipotential cardiac signals to continuously monitor cardiac activity of the subject.

8. The orogastric or nasogastric feeding tube as set forth in claim 1, further including:
an esophageal thermistor for monitoring a core temperature of the subject.

9. The orogastric or nasogastric feeding tube as set forth in claim 8, further including:
a plurality of electrodes spaced on an outside of the tubular structure for measuring cardiac activity of the subject.

10. The orogastric or nasogastric feeding tube as set forth in claim 9 wherein the tubular construction includes at least one of:
a molded or jacketed build-up of discrete parts including lumen, wires, electromechanical components;
wires layered onto a center lumen that is over-molded, cast, or encapsulated after layering;
molded in-wall wires in a single lumen or a multi-lumen extrusion; or
a discrete bundle of wires installed into one of multiple lumens, the multiple lumens physically separate a feeding path in one of the lumens from the thermistors.

11. The orogastric or nasogastric feeding tube as set forth in claim 2, wherein the monitor is connected to the wires, the monitor being configured to implement an algorithm which determines respiration rate and respiration depth from the relative temperature changes between the oropharynx thermistor and the hypopharynx thermistor.

12. The orogastric or nasogastric feeding tube as set forth in claim 11, wherein at least one of the thermistors is segmented into two or more segments with a gap between segments.

13. An esophageal feeding tube including:
a molded or jacketed build-up of discrete parts such as lumen, wires, or electromechanical components;
wire layered onto a center lumen that is over-molded, cast, or encapsulated after layering;
molded in-wall wires in a single lumen or a multi-lumen extrusion; or
a discrete wire bundle installed into one of multiple lumens, the multiple lumens physically separate a feeding path in one of the lumens from the electromechanical components;
a tubular construction defining at least one lumen that provides a pathway for nourishment from outside of a subject into a stomach or small intestine of the subject surrounded by a jacket;
at least one of:
fiber-optic filaments that provide light to a fiber optic window adjacent to the jacket that senses pulse and SpO2;
a soft molded tip that is attached to a distal end of the feeding tube;
a light source at the tip of the feeding tube for visually tracking the tip of the feeding tube; or
a distal electrode at the tip of the feeding tube for indicating when the tip of the feeding tube passes into the stomach of the subject;
at least two electrodes that are uniformly or non-uniformly spaced, on the outside of the tube for measuring cardiac activity of the subject, of which at least one electrode is used at any given time; and
a monitor which implements a monitoring algorithm to select which of the electrodes has an optimal signal, such that the algorithm can be implemented when the feeding tube is inserted or periodically as the subject grows and the feeding tube is repositioned.

14. A method of measuring a respiration flow rate, the method comprising:
inserting an orogastric or nasogastric feeding tube that defines at least one lumen that provides a pathway for nourishment into an esophagus of a subject;
advancing the feeding tube to a position estimated to place a tip of the feeding tube in a selected location in a stomach or small intestine of the subject to position an oropharynx thermistor in a region of a pharynx of the subject and a hypopharynx thermistor inferior to the pharynx of the subject;
sensing a temperature in the region of the subject's pharynx with the oropharynx thermistor:
sensing a temperature inferior to the subject's pharynx with the hypopharynx thermistor,
determining the respiration flow rate from a relative temperature change between the oropharynx thermistor and the hypopharynx thermistor.

15. The method as set forth in claim 14, further including:
verify the tip is in the stomach after insertion by measuring the pH at the tip.

\* \* \* \* \*